United States Patent [19]
Cox

[11] Patent Number: 5,695,484
[45] Date of Patent: Dec. 9, 1997

[54] ANAL PATCH FOR FECAL INCONTINENCE

[76] Inventor: Brian J. Cox, 10191 Lebanon Dr., Cupertino, Calif. 95014

[21] Appl. No.: 571,154

[22] Filed: Dec. 12, 1995

[51] Int. Cl.⁶ ........................................ A61F 5/44
[52] U.S. Cl. ..................... 604/304; 604/305; 604/307
[58] Field of Search ...................... 604/328, 304–307, 604/385.1, 387, 359, 355; 600/29–31; 607/41, 138

[56] References Cited

U.S. PATENT DOCUMENTS

| 4,209,009 | 6/1980 | Hennig. | |
|---|---|---|---|
| 4,445,899 | 5/1984 | Bond. | |
| 4,484,949 | 11/1984 | Sohn et al.. | |
| 4,561,435 | 12/1985 | McKnight et al. | 604/304 |
| 4,593,053 | 6/1986 | Jevne et al.. | |
| 4,850,986 | 7/1989 | Temple. | |
| 4,945,084 | 7/1990 | Packman. | |
| 4,979,947 | 12/1990 | Berman. | |
| 5,074,855 | 12/1991 | Rosenbluth et al. | 604/385.1 |
| 5,386,836 | 2/1995 | Biwas | 600/29 |

OTHER PUBLICATIONS

Clinical Assessment of the Anal Continence Plug, J. Christiansen MD & K. Roed–Petersen, MD., vol. 36, No. 8 Dis Colon Rectum, Aug. 1993, pp. 740–742.

*Primary Examiner*—John G. Weiss
*Assistant Examiner*—David J. Cho
*Attorney, Agent, or Firm*—William G. Lane, Inc., P.C.

[57] ABSTRACT

An anal patch for controlling fecal incontinence comprising a polymeric body member adapted to be fitted into the natal cleft about the anal opening and secured to the natal cleft with a releasable adhesive material.

18 Claims, 2 Drawing Sheets

ANAL PATCH FOR FECAL INCONTINENCE

FIELD OF THE INVENTION

This invention relates to the field of medical devices used to control fecal incontinence in patients. In particular, the present invention is directed to an anal patch removably attached to the natal cleft surrounding the anal opening for closure or damming of the anal opening.

BACKGROUND OF THE INVENTION

Fecal incontinence is an extremely uncomfortable, inconvenient and embarrassing condition from which a substantial number of human beings suffer due to disease, such as nerve compression impairment or degeneration, surgical impairment due to radical surgery in the lower spine or in the anal or rectal zones of the body, injury such as spinal column injuries, or old age. A number of solutions to this problem have been suggested, unfortunately none of them have been successful enough to be utilized commercially. At the present time, most people that suffer from fecal incontinence wear large diapers and/or plastic or rubber underpants and practice bowel control by dietary control and a bowel release regimen to prevent soiling and odors associated with fecal incontinence. Fecal incontinence has a number of serious hygienic problems associated with it which requires constant monitoring. People suffering from fecal incontinence normally require the attendance of a nurse or other medical helper once a day.

SUMMARY OF THE INVENTION

The present invention, in its broadest terms, comprises a pad having a biocompatible adhesive on one side. The pad is adapted to be inserted into the natal cleft about the anal opening to form a removable seal having sufficient adhesive power to occlude the anal opening and prevent the leakage or discharge of fecal material. The use of the anal patch permits the patient suffering from fecal incontinence to develop a bowel movement regimen, so that the patient can have a better quality of life. Such a regimen is considered therapeutic and healthful since it ferments the colon and the rectum areas to reabsorb moisture from the fecal material in a matter that is considered normal for human discharge to develop firm stools. It has been found that patients who suffer from fecal incontinence have a tendency to discharge watery stools causing the loss of water and nutrients to the body. The formation of firm stools in the rectum and colon also improves the tone of these organs to exhibit peristaltic muscle contractions.

Although the anal patch or the present invention can be a flat sheet like patch, it is preferably a shaped patch which is adapted to fit in the natal cleft about the anal opening so as to yield a more comfortable patch for the patient. Preferably the anal patch is formed from a soft, but strong, foam material, especially a polyurethane base foam material coated with a biocompatible adhesive on one side. The adhesive side makes contact with the external tissue of the natal cleft to form a seal about the anal opening. In some instances, it may be desirable to have a fluid impermeable film or membrane positioned either between the adhesive and the patch backing or body material or on the back side of the backing material wherein the front side of the backing material has the adhesive coating. The front side of the patch is the side facing the anal opening and the back side is the side of the patch opposite the front side.

The adhesive coating can coat the entire side of one surface or it can be positioned on the periphery zone of the patch leaving a center portion of the patch adhesive free which will be positioned about the anal opening.

The patch will be supplied with an adhesive release sheet which protects the adhesive prior to use of the patch and which can be easily removed from the adhesive layer at the time of application.

The backing layer and/or the adhesive layer, or additional layers applied to the backing layer, either between the adhesive coating and the backing layer or on the front side of the backing layer can contain additional agents such as anti-fungal agents, anti-bacterial agents, anti-viral agents, anti-inflammatory agents, anti-itching agents, humicants, moisture absorbing agents, gas absorbing agents, buffering agents for pH control, drying agents or the like. Additionally, the patch may contain fluid absorbing materials such as hydrophilic agents such as starch, cellulose, hydrophilic polymers, or hydrophilic salts such as anhydride calcium sulfate. The patch may also be compounded with odor absorption material such as activated carbon, desiccant silica gel, and the like, to absorb fluids and odors from fecal discharges and the natal cleft skin.

In another embodiment of the present invention, the patch will have a gas pressure release means situated in the patch to permit the escape of gas from the intestinal tract. The gas release means will comprise a gas permeable membrane positioned in the portion of the patch which will be centered near the anal opening. The gas permeable membrane will permit the passage of gas but inhibit the passage of fluids and solids.

In one embodiment of the invention, the patch will incorporate a tab to aid in the removal of the patch from natal cleft. The tab permits the patch to be gently peeled away from the external tissue of the natal cleft. Because of the design of the patch, the direct pulling off of the patch from the natal cleft would involve shearing the adhesive bond of the adhesive coating from the external skin of the natal cleft. The shearing bonding strength of the patch in the natal cleft is very high whereas the tensile bond of the adhesive coating and the external skin is less and allows the patch to be peeled away from the natal cleft.

In another embodiment of the present invention, the anal patch will be made of biodegradable polymeric materials and/or paper based materials with the adhesive being a biodegradable polymeric material.

In another embodiment of the present invention, the anal patch would incorporate a protrusion or nipple in its front side adopted to be received in or engage the anal opening for purposes of creating a better seal for occlusion of the anal opening and for the optional purpose of permitting medicinal agents, such as for treatment of hemorrhoids, anti-inflammatory agents, and the like to be incorporated in the protrusion for direct contact with the tissue of the anal opening to permit diffusion of the medicinal agents into the tissue.

DETAILED DESCRIPTION

Figure 1:
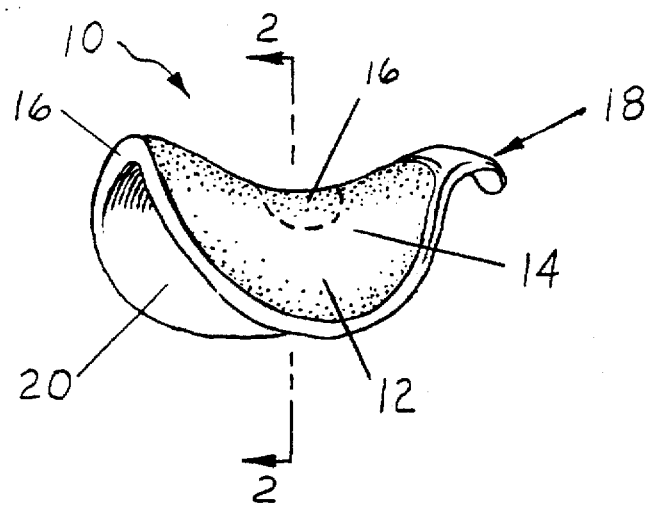
FIG. 1 is perspective view of the anal patch for fecal incontinence according to the present invention.

Referring to FIG. 1, the anal patch 10 has a generally saddle shape with an adhesive coating 12 on the front side 14 of the body member 16 adapted to adhere to the skin within the natal cleft with the saddle point region 24 of the body member located about the anal opening. At one end of the anal patch, there is a pull tab 18 adapted to be grabbed by fingers in order to either place the anal patch in the natal cleft or to remove the anal patch. The back side 20 of the body member 16 has a smooth rubber-like consistency and is impermeable to gas and fluids and is a barrier to the escape of fluids and gases from the anal opening.

The adhesive coating 12 can extend over the entire front side 14 or around the peripheral zone of the front side leaving an area free of adhesive in the center about the area where the patch will contact the anus. The adhesive free area 13 is demarcated with a dotted line in FIGS. 1, 3, 4 and 5.

The body member is preferably molded from a polymeric material that is compatible with the body tissues. Appropriate polymeric materials include foams formed from water actuation of pre-polymers based on either toluene diisocyanate (TDI) or methylene diphenyl diisocyanate (MDI). Such pre-polymers are supplied by W.R. Grace & Company under the trademarks "HYPOL" and "HYPOL PLUS". The body member can also be made of a biodegradable material, such as cellulose, polyactic acid or cotton fiber which have been treated to make them gas impervious and fluid impermeable. A polyurethane foam can also be used which has been rendered biodegradable by hydrolysis of a weak backbone link, such as an amine group. Other foam materials, such as polyolefins, can be used and made hydrolytically biodegradable by using weak links such as starches in the polymer backbones.

Any tissue compatible adhesive coating can be employed including those comprising the pressure-sensitive hydrophilic hydrogel adhesive materials. Such hydrogel adhesives are marketed by Promeon Division Medtronic, Inc., of Minneapolis, Minn. under the trademark "PROMEON". The hydrogel compositions disclosed in Jevne et al U.S. Pat. No. 4,593,053 can be used in the invention. The disclosure of that patent is incorporated herein by reference. Another type of adhesive coating that can be used is a mixture of poly 2-hydroxyethyl methacrylate (pHEMA) and polyethylene glycol (PEG) as a plasticizer. The percentage of pHEMA may range from about 45 to about 75% by weight, with a corresponding range of PEG of about 55 to about 25% by weight. The preferred composition is about 53 to about 54 wt. % pHEMA and about 47 to about 46 wt. % PEG. Lower percentages of pHEMA yield greater adhesiveness while higher percentages of pHEMA yield greater durability. The PEG has a molecular weight between about 400 and about 1,000, with 400 preferred. The pHEMA is preferably a mixture of low molecular weight pHEMA between about 10,000 and 100,000 and high molecular weight pHEMA which is greater than about 100,000. The low molecular weight pHEMA provides good adhesive properties, While a high molecular weight pHEMA improves adhesive structural integrity. The pHEMA mixture is preferably between about 10 to 50% by weight low molecular weight pHEMA and the balance being high molecular weight pHEMA with precise portions of the mixture being determined by the particular adhesive properties desired.

The adhesive can be an organic solvent plasticized water soluble polymer, such as a methyl cellulose-based material combined with a water soluble polymer.

While the preferred plasticizer is PEG, as described above, other plasticizers can be used, such as propylene glycol, polypropylene glycol or glycerin.

If the body member is made of TDI or MDI, the material of the body itself can be rendered adhesive by combining the TID or MDI one to one by weight with about 0.25 to about 0.5 molar ammonium hydroxide during the water actuation of the foam. The material has a surface that is positively charged so that it will adhere to negatively-charged mucoid surfaces. Frequently the skin surface of the natal cleft is negatively charged.

The adhesive coating not only provides the seal preventing the leakage of discharges from the anal opening from beyond the anal patch, but the adhesive coating also maintains the anal patch in place during usage. The adhesive coating must be relatively strong, because it is envisioned that in the preferred embodiment of the present invention, the anal patch will be worn for at least 3 hours and preferably 24 hours between each patient's bowel movement. When the patient first undergoes bowel control training to establish a bowel movement regimen, the anal patch may be changed more frequently. As the patient learns to control his or her bowel movements, the anal patch will be changed less and less frequently and finally the patient will be able to utilize an anal patch for periods up to 24 hours. In such situations, the anal patch may be subject to elevated fluid pressures of up to about 150 centimeters of water or higher. Pressures exceeding 150 centimeters of water normally exert such pressures to the digestive tract, that the patient is not able to withstand the discomfort or pain and normally will desire to relief themselves to relieve the pressure.

Figure 3:
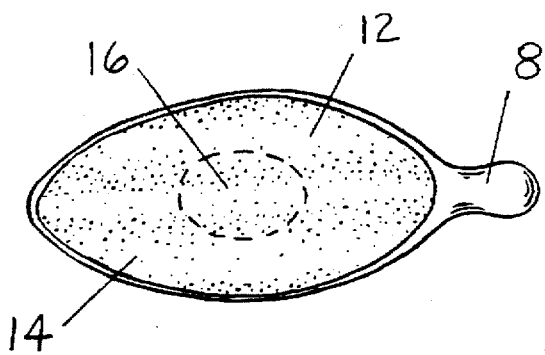
FIG. 3 is a top view of the anal patch of FIG. 1.

FIG. 3 is a top view of anal patch of FIG. 1 showing the tab 18 extending from one end of anal patch 10.

Figure 4:
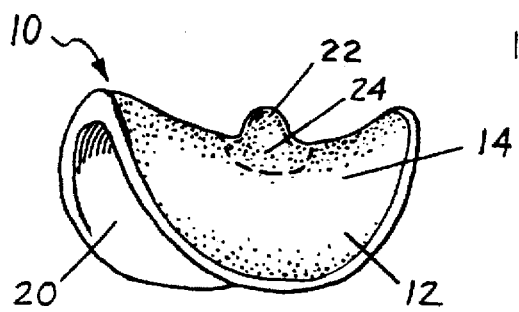
FIG. 4 is a perspective view of another embodiment of the anal patch of the present invention.

An alternative embodiment of the invention is illustrated in FIG. 4. The anal patch 10A has a nipple 22 located in the saddle point region 24 of the front side 14 of the anal patch 10a. The nipple is designed to fit into and be received within the anal opening. It can also aid in closure of the anal opening.

In one embodiment of the invention, the nipple 22 can be impregnated with therapeutic compositions, such as antibiotics, anti-inflammatories, anti-hemorrhoidal agents and anti-itching compounds. The nipple can be coated or not coated with an adhesive coating 12. The nipple can be compounded from relatively hard rubber-like material or a soft rubber-like material depending upon its intended purpose.

A number of anti-bacterial or germicidal agents can be employed in the body member or in the adhesive coating, such as silver oxide or silver azide.

Although not shown, the anal patch can include a highly absorbent hydrophilic layer between the adhesive coating and the body member. The hydrophilic layer is preferably a mixture of pHEMA/PEG adhesive and a micro sponge material, such as carboxyl methyl cellulose (CMEC). The hydrophilic layer draws moisture from the adhesive layer and absorbs the moisture, thereby prolonging the useful life of the adhesive by delaying moisture saturation of the adhesive. Absorption of moisture causes the hydrophilic layer to swell which may enhance the sealing properties of the anal patch.

Figure 2:
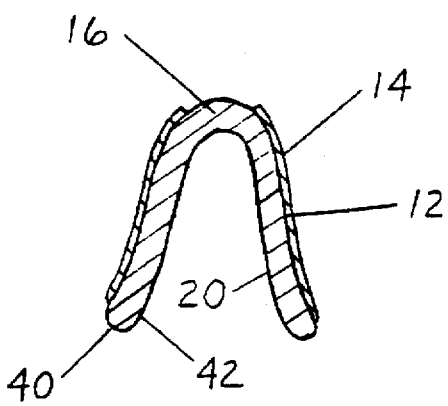
FIG. 2 is cross sectional view taken along lines 2—2 of FIG. 1.
Figure 5:
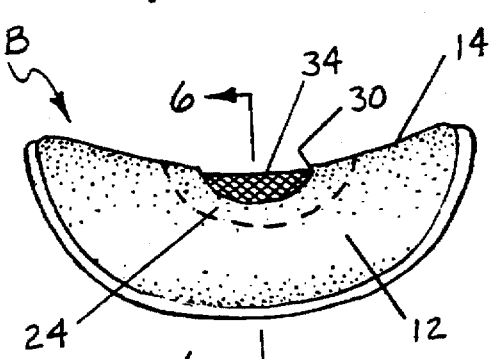
FIG. 5 is a side view of another embodiment of the anal patch of the present invention.
Figure 6:
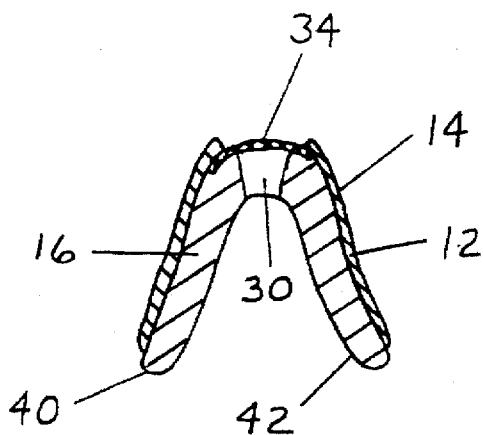
FIG. 6 is a cross sectional view taken along line 6—6 of FIG. 5.

FIG. 5 and FIG. 6 show another alternative embodiment of the present invention wherein anal patch 10B has a orifice 30 extending through body member 16 of the anal patch in the region of the saddle point 24. A gas permeable, fluid impermeable membrane 34 seals off the orifice 30 to prevent the escape of fluids from the anal opening when the anal patch is applied to the natal cleft. Although the membrane 34 is impermeable to fluids, it is gas permeable and prevents gas build up which discharges through the anal opening by permitting the gas to escape through the membrane. The front side 14 of the anal patch has an adhesive coating 12 similar to the adhesive coating of the anal patch described in FIGS. 1–3. The gas permeable membrane can be a fabric, metallic or polymeric membrane which is hydrophobic to resist the passage of aqueous solutions through the membrane. Preferably the membrane will be a micro or millipore membrane which will only permit gaseous molecules to pass through.

In one embodiment of the invention, the gas permeable membrane will be compounded or coated with a metallic material, such as silver oxide or copper oxide or copper metal which would react with sulfur compounds being emitted with gaseous materials from the anal opening as a means of odor control. Alternatively, the gas permeable membrane can be compounded with activated carbon to absorb odoriferous gaseous discharges from the digestive tract.

Figure 7:
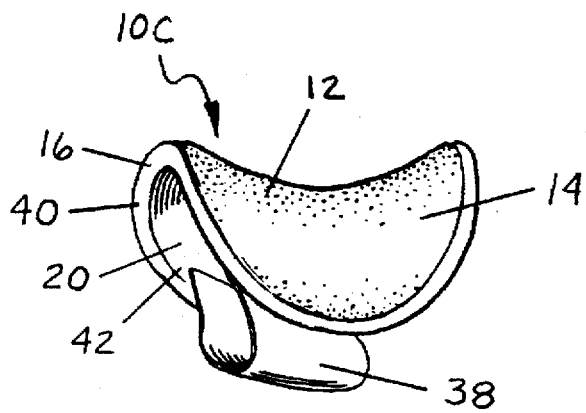
FIG. 7 is a perspective view of another embodiment of the anal patch of the present invention.

FIG. 7 illustrates another embodiment of the present invention wherein the anal patch 10C has attached to its back side 20, a flexible finger strap 38. The finger strap permits the user of the anal patch to easily grasp the anal patch for application to and removal from the natal cleft. The flexible strap 38 can be made of fabric or polymeric material similar to the material used in body member 16. The strap is attached at its opposite ends to opposite sides of the back side 20 of the anal patch at the outer edges 40 of the anal patch or at the peripheral margin 42 of the anal patch (see FIG. 2).

Figure 8:
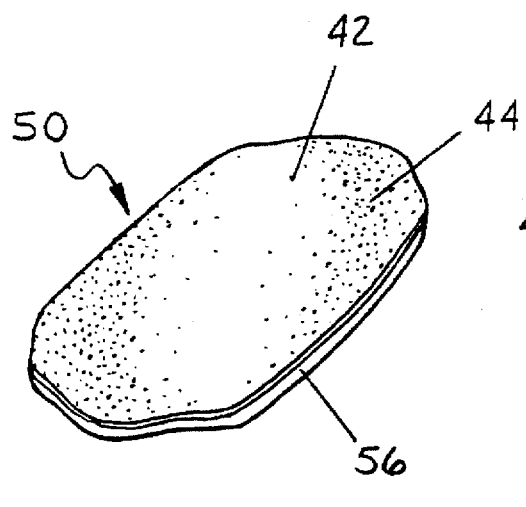
FIG. 8 is a perspective view of a flat planar anal patch of the present invention.
Figure 9:
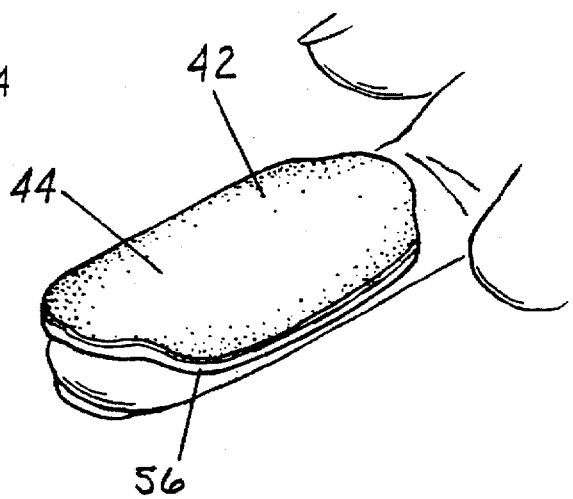
FIG. 9 is a perspective view of the anal patch of FIG. 8 positioned on the finger for application to the patient.

FIGS. 8 and 9 illustrate another alternative embodiment of the present invention wherein the anal patch 50 is a flat flexible patch which can be fitted into the natal cleft about the anus with the finger when positioned as shown in FIG. 9. The top surface 42 of the patch has an adhesive coating 44 very similar to the adhesive coating used in the other natal patch such as the natal patch illustrated in FIGS. 1 through 3. The adhesive coating can extend over the entire top surface or over the peripheral region leaving an adhesive free zone that contacts the anus as described for patches 10, 10A and 10B. The body member of the natal patch 56 is made of a polymeric compound similar to the material used in the body members 15 for the other anal patches described above. The material is flexible and impermeable to gas and fluid for incontinence control. The patch can have an orifice (not shown) sealed off with a gas permeable fluid impermeable membrane as the anal patch shown in FIGS. 5 and 6.

In the preferred embodiment of the present invention, the backing material 15 and 46 of the anal patch is a sealed cell polymeric foam material. However, non-foamed polymeric may also be employed. Preferably the material used for the body member of the anal patch has good tensile and shear strength and is compressible to provide the maximum comfort to the wearer.

The flat flexible patch 50 can have a raised nipple (not shown) similar to nipple 22 on patch 10A. The flat flexible patch can also have a tab extending out from a side edge (not shown) like tab 18 of patch 10.

The anal patch can also include a scrim layer (not shown) which can be enclosed within the adhesive coating applied to the body member. The scrim layer is preferably a thin, non-woven sheet of polyester that would reinforce elastomeric material of the body member. However, the scrim layer can be any woven or non-woven fabric with open or closed mesh. The scrim layer would add structural integrity to the adhesive coating thereby enhancing the durability of the anal patch. The scrim layer can be placed in the adhesive coating before the coating is cured to a semi-solid or the scrim layer can be applied to the front side of the body member before the adhesive coating is applied and the scrim layer would be sandwiched between the adhesive coating and the front side of the body member. Optionally, the scrim layer can be incorporated in the body member or attached to the back side of the body member.

Specific embodiments of the present invention have been illustrated in the drawings and described herein. However, other modifications of the invention comprising the same elements described are intended to be part of this invention. Thus, the shape and design of the anal patch and the polymers and adhesive used in its manufacture can be modified to achieve maximum incontinence control and at the same time give the wearer the maximum degree of comfort as well as security.

What is claimed:

1. An anal patch comprising a saddle-shaped body member having a peripheral edge, front side and a back side adapted to be received in a natal cleft about an anal opening; the front side having a saddle shaped and in adhesive contact with the skin of the natal cleft, the front side of the body member having a central area surrounded by a peripheral region about the outer margin of the front side, the front side constituting the top of the saddle shaped body member; an adhesive coating on the surface of the front side of said body member on the peripheral region for releasably securing said body member to the skin of the natal cleft to form a seal about the anal opening to prevent the release of discharges from the anal opening, the central area of the front side of the body member free of the adhesive coating.

2. The anal patch according to claim 1 wherein the body member is impervious to fluids, moisture and gases.

3. The anal patch according to claim 1 wherein the adhesive is moisture and fluid resistant.

4. The anal patch according to claim 1 wherein the adhesive coating contains at least one medicinal agent.

5. The anal patch according to claim 1 wherein the body member is compounded with at least one medicinal agent.

6. The anal patch according to claim 5 wherein the medicinal agent is an antibiotic.

7. The anal patch according to claim 5 wherein the medicinal agent is an anti-inflammatory.

8. The anal patch according to claim 5 wherein the medicinal agent is an anti-fungal agent.

9. The anal patch according to claim 5 wherein the medicinal agent is an anti-itching agent.

10. The anal patch according to claim 1 wherein the body member is compounded with odoriferous absorbing material.

11. The anal patch according to claim 1 wherein the body member is compounded with a moisture absorbing agent.

12. The anal patch according to claim 1 wherein the body member has a pull tab extension extending from the peripheral edge adapted to be grabbed for insertion and removal of the anal patch from the natal cleft.

13. The anal patch according to claim 1 wherein the body member has a raised nipple extending upwardly from the front side of the body member in the central area of the front side of the body member adapted to be received within the anal opening.

14. The anal patch according to claim 13 wherein the raised nipple is compounded with a medicinal agent.

15. The anal patch according to claim 1 wherein the body member has a bore extending from its back side to its front side in the saddle point region of the body member, and a gas permeable fluid impervious element sealing off the bore and adapted as a gas release means for releasing gaseous discharges from the anal opening.

16. The anal patch according to claim 1 including a strap secured to the back side of the body member and adapted to receive and detachably secure a finger for application and removal of the anal patch from the natal cleft.

17. The anal patch according to claim 16 wherein the strap has opposite ends, the opposite ends of the strap are attached to opposing peripheral edges of the body member.

18. An anal patch comprising a flat planar body member having a front side and a back side, the front side adapted to receive in a natal cleft about an anal opening with the front side of the body member in contact with the skin of the natal cleft, an adhesive coating on the surface of the front side of the body member for releasably securing said body member to the skin of the natal cleft to prevent release of discharges from the anal opening; and a raised nipple extending upwardly from the front side of the body adapted to receive within the anal opening.

* * * * *